(12) United States Patent
Lee

(10) Patent No.: US 8,986,756 B2
(45) Date of Patent: Mar. 24, 2015

(54) COMPOSITION COMPRISING THE EXTRACT OF COMBINED HERBS FOR PREVENTING AND TREATING LIVER DISEASE

(76) Inventor: Jung Sik Lee, Seoul (KR)

( * ) Notice: Subject to any disclaimer, the term of this patent is extended or adjusted under 35 U.S.C. 154(b) by 1262 days.

(21) Appl. No.: 12/520,534

(22) PCT Filed: Dec. 18, 2007

(86) PCT No.: PCT/KR2007/006648
§ 371 (c)(1),
(2), (4) Date: Jun. 19, 2009

(87) PCT Pub. No.: WO2008/075888
PCT Pub. Date: Jun. 26, 2008

(65) Prior Publication Data
US 2010/0092584 A1    Apr. 15, 2010

(30) Foreign Application Priority Data

Dec. 20, 2006  (KR) .......................... 10-2006-0130518
Dec. 17, 2007  (KR) .......................... 10-2007-0132451

(51) Int. Cl.
| | | |
|---|---|---|
| A61K 36/79 | (2006.01) | |
| A61K 36/282 | (2006.01) | |
| A61K 36/06 | (2006.01) | |
| A61K 36/481 | (2006.01) | |
| A61K 36/07 | (2006.01) | |
| A23L 1/30 | (2006.01) | |

(52) U.S. Cl.
CPC ............... *A61K 36/07* (2013.01); *A23L 1/3002* (2013.01); *A61K 36/282* (2013.01); *A61K 36/481* (2013.01); *A61K 36/79* (2013.01); *A23V 2002/00* (2013.01)

USPC ...... 424/740; 424/725; 424/195.15; 424/777; 424/779

(58) Field of Classification Search
None
See application file for complete search history.

(56) References Cited

U.S. PATENT DOCUMENTS

2005/0238654 A1* 10/2005 Takeda ...................... 424/195.15
2006/0171958 A1*  8/2006 Stamets ................... 424/195.15

FOREIGN PATENT DOCUMENTS

| CN | 1284348 A | * | 2/2001 |
|---|---|---|---|
| CN | 1470271 A | * | 1/2004 |
| JP | 57147433 A | * | 9/1982 |
| JP | 59036623 A | * | 2/1984 |
| JP | 01165583 A | * | 6/1989 |
| KR | 9405600 B1 | * | 6/1994 |
| KR | 2004043707 A | * | 5/2004 |
| KR | 2005000229 A | * | 1/2005 |
| KR | 2005116007 A | * | 12/2005 |
| WO | WO 2004096252 A1 | * | 11/2004 |

* cited by examiner

*Primary Examiner* — Chris R Tate
*Assistant Examiner* — Deborah Davis
(74) *Attorney, Agent, or Firm* — Kirk Hahn

(57) ABSTRACT

The present invention is related to a combined herb composition comprising herbs of *Coriolus versicolor*, *Astragalus membranaceus Bunge*, and additionally comprising at least one herb selected from group consisting of *Schisandra chinensis*, and *Artemisia capillaris*, according to the need for the prevention and treatment of liver disease and methods of using the above crude drug composition and pharmaceutical composition as hepato-protective agent.

11 Claims, 17 Drawing Sheets

COMPOSITION COMPRISING THE EXTRACT OF COMBINED HERBS FOR PREVENTING AND TREATING LIVER DISEASE

This application is the U.S. National Phase under 35 U.S.C. §371 of International Application PCT/KR2007/006648, filed on Dec. 18, 2007, which claims priority to Korean Patent Application No. 10-2007-0132451, filed on Dec. 17, 2007 and Korean Patent Application No. 10-2006-0130518, filed on Dec. 20, 2006. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention is related to a composition comprising the herb extract of *Coriolus versicolor*, *Astragalus membranaceus Bunge*, *Schisandra chinensis* and *Artemisia capillaris*, according to the need for the prevention and treatment of liver diseases, and methods of using the above crude drug composition and pharmaceutical composition as a hepato-protective agent.

BACKGROUND ART

Liver disorders are one of the most frequently occurring diseases in present human being exposed by various unfavorable environments for example, polluting substance, toxic substance such as overdrinking, smoke etc. as well as psychological stress, which could be recovered by rest however it could be severed to give rise to other disease such as the disorder of immune system. There have been reported that toxic substance such as carbon tetrachloride, D-galactosamne etc. causes to toxic in liver and kidney resulting from the injury of cellular membrane (Brucker, J. V., Fund. Appl. Toxicology, 6, pp 16-34, 1986).

Several drugs derived from natural product resource acting with the inhibition of free radical reproduction have been reported till now, for example, silymarin (SLM) isolated from the fruit of *Silybum marianum* (*Carduus marianus*) belong to Compositae, BDD (Biphenyl Dimethyl Dicarboxylate), a synthetic analog of schizandrin isolated from *Schisandra chinensis* etc. (Caragy A. B., Food Technology, 46, pp 65-68, 1992; Liang jun, Y., et al., Biochem. And Biophy. Res. Comm., 212, pp 360-366, 1995).

However, there has been a need for the development of effective and safe drugs to treat and prevent liver diseases or improving liver function till now.

*Corilous versicolor*, a mushroom belonging to Aphyllophorales distributed in all the world has been reported to comprise ergosterol, beta-sitosterol, coriolan, krestin-D-glucan and thelphoric acid and to show anti-bacterial activity, anti-inflammatory activity, immune enhancing activity, cholesterol-lowering activity and so on (Park Wan-Hee and Lee Ho-Deuk, Illustrated Book of Korean Medicinal Mushrooms, Kyo-Hak Publishing Co., Ltd, p 472, 1st Ed. 1999)

*Astragalus membranaceus Bunge* belonging to Leguminosae has been reported to comprise formononetin, isoliquiritigenin, glucuronic acid, choline, betaine, folic acid, 2',4'-dihydroxy-5,6-dimethoxy-isoflavone, kumatakenin and etc. and to show cardiac action, blood pressure lowering activity, diuretic activity, hormonal like activity and etc. (Chung, B. S., et al., Illustrated Crude Drug Encyclopedia, Youngrim Publishing Co. Ltd., 2nd Ed., p 662-664, 1998; http://www.tradimed.com).

*Schisandra chinensis* belonging to Magnoliaceae has been reported to comprise Scizandrin, gomisin A-Q, citral, alpha-ylangene, citric acid, malic acid, beta-chamigrene, fatty oil, deoxyschizandrin and etc. and to show vasodilating activity, blood pressure lowering activity, expectorant activity and etc. (Chung, B. S., et al., Illustrated Crude Drug Encyclopedia, Youngrim Publishing Co. Ltd., 2nd Ed., p 471-473, 1998; http://www.tradimed.com).

*Artemisia capillaris* belonging to Compositae has been reported to comprise scoparone, chlorogenic acid, caffeic acid, pinene, capipillin, capillene, capillarin, stearic acid, palmitic acid and etc. and to show blood pressure lowering activity, diuretic activity, cholagogue activity and etc. (Chung, B. S., et al., Illustrated Crude Drug Encyclopedia, Youngrim Publishing Co. Ltd., 2nd Ed., p 1016-1018, 1998; http://www.tradimed.com).

However, there has been not reported or disclosed about therapeutic effect of combined herb extract described above on liver disease in any of above cited literatures, the disclosures of which are incorporated herein by reference.

Therefore, the present inventors have endeavored to find the effective herbal formulation for enhancing hepato-protective efficacy and to study the pharmacological effect of the above mentioned combined herbal extract and finally, the present inventors have found that the combined crude drug described above is effective in preventing and treating liver diseases as a hepato-protective agent.

DISCLOSURE

Technical Problem

According to one aspect, the present invention provides a pharmaceutical composition comprising the extract of combined herbs with *Coriolus versicolor*, *Astragalus membranaceus Bunge*, *Schisandra chinensis* and *Artemisia capillaris* for preventing and treating liver diseases.

The present invention also provides pharmaceutical compositions comprising the above-mentioned extract as an active ingredient in an effective amount to prevent and treat liver diseases, together with a pharmaceutically acceptable carrier.

The present invention also provides a method for treating liver diseases by protecting hepatic cell in a mammal by administering to said mammal an effective amount of above-mentioned extract, together with a pharmaceutically acceptable carrier thereof.

The present invention also provides a use of the above described extract for the manufacture of medicament employed for treating or preventing liver disease in human or mammal.

The present invention also provides a health functional food comprising the above described extract for the prevention or improvement of liver disease by protecting hepatic cell as an active ingredient in an effective amount to prevent and improve liver disease.

Technical Solution

Accordingly, it is an object of the present invention to provide a pharmaceutical composition comprising the extract of combined herbs consisting of *Coriolus versicolor* and *Astragalus membranaceus Bunge*, as an active ingredient in an effective amount to prevent and treat liver diseases, together with a pharmaceutically acceptable carrier.

The present invention also provides a pharmaceutical composition comprising the extract of combined herbs additionally comprising at least one herb selected from the group consisting of *Schisandra chinensis* and *Artemisia capillaris* besides the above-mentioned combined herbs for preventing and treating liver diseases.

It is another object of the present invention to provide a use of the above-described extract for the manufacture of medicament employed for treating or preventing liver disease in human or mammal.

It is the other object of the present invention to provide a method for treating liver diseases by protecting hepatic cell in a mammal by administering to said mammal an effective amount of the above-mentioned extract, together with a pharmaceutically acceptable carrier thereof.

In a preferred embodiment of the invention, the extract disclosed herein comprises the extract of combined herbs, i.e., *Coriolus versicolor* and *Astragalus membranaceus* Bunge, with the mixed ratio based on the dried weight of each herb (w/w %) ranging from 0.1-10:1, preferably, 0.5-5:1, more preferably 1-2:1, further more preferably, in the present invention to prevent or treat liver disease.

In a preferred another embodiment of the invention, the extract disclosed herein comprises the extract of combined herbs, i.e., *Coriolus versicolor, Astragalus membranaceus* Bunge and *Schisandra chinensis*, with the mixed ratio based on the dried weight of each herb (w/w %) ranging from 0.1-10:0.1-10:1, preferably, 0.5-5:0.5-5:1, more preferably, 1-2:1-2:1, further more preferably in the present invention to prevent or treat liver disease.

In a preferred the other embodiment of the invention, the extract disclosed herein comprises the extract of combined herbs, i.e., *Coriolus versicolor, Astragalus membranaceus* Bunge and *Artemisia capillaris*, with the mixed ratio based on the dried weight of each herb (w/w %) ranging from 0.1-10: 0.1-10:1, preferably, 0.5-5:0.5-5:1, more preferably, 1-2:1-2: 1, further more preferably in the present invention to prevent or treat liver disease.

In a preferred the other embodiment of the invention, the extract disclosed herein comprises the extract of combined herb i.e., *Coriolus versicolor, Astragalus membranaceus* Bunge, *Schisandra chinensis* and *Artemisia capillaris*, with the mixed ratio based on the dried weight of each herb (w/w %) ranging from 0.1-10:0.1-10:0.1-10:1, preferably, 0.5-5: 0.5-5:0.5-5:1, more preferably, 1-2:1-2:1-2:1:1, further more preferably, in the present invention to treat or prevent liver disease.

In accordance with one aspect of the present invention, there provided a health functional food comprising the above described extract for the prevention or improvement of liver disease by protecting hepatic cell as an active ingredient in an effective amount to prevent and improve liver disease.

The "liver disease" disclosed herein comprises fatty liver, acute or chronic hepatitis, hepatomegaly, hepatophyma, hepatocirrhosis and liver cancer, preferably, fatty liver, hepatocirrhosis and hepatitis, more preferably, alcoholic fatty liver, non-alcoholic fatty liver, diabetic fatty liver and hepatitis.

The herbs, which can be used in the present invention, include the same genus plants which would be apparent to those skilled in the art and have be used for identical or similar purpose and can be substituted for the prevention and treatment of liver diseases.

Inventive composition of the present invention is used in the form of pulverized form thereof, extracted form therefrom or dried extract form thereof.

The above extracted form of crude drug composition can be obtained by extracting with distilled water, lower alcohols such as methanol, ethanol and the like or the mixtures thereof, preferably water.

The term "extract" disclosed herein comprises crude extract, lower alcohol insoluble fraction extract and non-polar solvent soluble extract.

The term "crude extract" disclosed herein comprises the extract soluble in distilled water, C1-C4 lower alcohols such as methanol, ethanol and the like or the mixtures thereof, preferably the mixture solution with ethanol and water, more preferably, 50-90% ethanol solution in water.

The term "lower alcohol insoluble fraction extract" disclosed herein comprises the extract prepared by the steps: extracting the crude extract with lower alcohol solution such as the mixture solution with ethanol and water, more preferably, 50-90% ethanol solution in water to fractionate into the lower alcohol soluble fraction and lower alcohol insoluble fraction; and collecting the lower alcohol insoluble fraction extract of the present invention.

The term "non-polar solvent soluble extract" disclosed herein comprises the extract prepared by the steps: fractionating the crude extract with non-polar solvent such as hexane, chloroform, dichloromethane or ethylacetate, preferably, hexane; and collecting the non-polar solvent soluble extract of the present invention.

In the most preferable embodiment of the present invention, the "extract" of the combined herbs consists of a crude extract of *Coriolus versicolor*, lower alcohol insoluble fraction extract of *Astragalus membranaceus* Bunge and *Artemisia capillaris* and non-polar solvent soluble extract of *Schisandra chinensis*, in the inventive composition but it is not intended to limit thereto.

The pharmaceutical composition for treating liver diseases could contain about 0.01 to 95 w/w %, preferably 0.5 to 80 w/w % of the above herb composition of present invention based on the total weight of the composition.

An inventive herb composition may be prepared in accordance with the following preferred embodiment.

For the present invention, the above crude drug composition can be prepared by following procedure; the herbs, i.e., *Coriolus versicolor, Astragalus membranaceus* Bunge, *Schisandra chinensis* and *Artemisia capillaris* are washed, sliced, dried, and mixed with appropriate ratio (w/w). Above mixture thereof is pulverized to obtain the pulverized form of crude drug composition.

The above pulverized crude drug composition is mixed with 5 to 20-fold, preferably, 10 to 15-fold volume of distilled water, alcohols such as methanol, ethanol and the like or the mixtures thereof, preferably, distilled water or the mixture of ethanol and water; and is enfleuraged at the temperature ranging from 0 to room temperature, preferably from 4 to 6° C., for the period ranging from 12 to 48 hours, preferably 20 to 24 hours or heated with reflux extraction at the temperature ranging from 80 to 120° C., preferably above 100° C., for the period ranging from 1 to 24 hours, preferably 2 to 5 hours with 2 to 5 times, or extracted by sonication, reflux or conventional extraction to obtain an aqueous extract form of crude drug composition.

Additionally, the herbal extract is filtered and concentrated at 80 to 90° C. under reduced pressure. The extract is concentrated by azeotropic distillation with volume of 10 to 60-fold water, 1 to 5 times and then dried by freeze drying or vacuum drying to obtain a dried crude extract of crude drug composition.

The inventive "lower alcohol insoluble fraction extract" of respective herb can be prepared by the steps: extracting the crude extract prepared the above-described step with lower alcohol solution such as the mixture solution with ethanol and water, more preferably, 50-90% ethanol solution in water in an amount ranging from 1 to 8 folds weight based on the weight of crude extract by being left alone in room temperature for the period ranging from 12 to 48 hours, preferably, 18 to 24 hours to fractionate into the lower alcohol soluble fraction and lower alcohol insoluble fraction; and collecting the lower alcohol insoluble fraction extract of the present invention.

The inventive "non-polar solvent soluble extract" of respective herb can be prepared by the steps: fractionating the crude extract prepared the above-described step with non-polar solvent hexane, chloroform, dichloromethane or ethylacetate, preferably, hexane in an amount ranging from 1 to 8 folds volume, preferably, 2 to 5 folds volume based on the volume of crude extract; and collecting the non-polar solvent soluble extract of the present invention.

It is another object of the present invention to provide a process for preparing the extract of the present invention as described above for the preparation of effective composition in preventing or treating liver diseases.

It is still another object of the present invention to provide a pharmaceutical composition comprising the pulverized form, extracted form or dried extract form of above crude drug extract obtained by above the described process as an active ingredient for preventing and treating liver diseases.

The inventive composition of the present invention prepared by the above-described process significantly inhibits the level of GOT, GPT, LDL-cholesterol, gene-expression of HMG-CoA reductase in hepatic tissue, liver fibrosis in rat experimental model as well as increases the level of blood HDL-cholesterol. When the oral acute toxicity of the extract was tested, the extract had no apparent effect on mortality, clinical signs, body weight changes and gross findings at necropsy.

The pharmaceutical composition for treating liver diseases could contain about 0.01 to 95 w/w %, preferably 0.5 to 80 w/w % of the above described crude drug composition of present invention based on the total weight of the composition.

It is another of the present invention to provide a hepatoprotective agent comprising the above described extract as an active ingredient in an effective amount to prevent and treat liver diseases.

It is another of the present invention to provide a method of treating of liver diseases in a mammal by administering to said mammal an effective amount of the above described inventive extract and pharmaceutically acceptable carrier thereof.

The inventive composition may additionally comprise conventional carrier, adjuvants or diluents in accordance with a using method. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The crude drug composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents, which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

Pharmaceutical formulations containing crude drug composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), suppository, or sterile injectable preparation (solution, suspension, emulsion).

The crude drug composition of the present invention in pharmaceutical dosage forms may be used in the form of their pharmaceutically acceptable salts, and also may be used alone or in appropriate association, as well as in combination with other pharmaceutically active compounds.

The desirable dose of the inventive composition varies depending on the condition and the weight of the subject, severity, drug form, route and period of administration, and may be chosen by those skilled in the art. However, in order to obtain desirable effects, it is generally recommended to administer at the amount ranging 0.01-10 g/kg, preferably, 1 to 5 g/kg by weight/day of the inventive composition of the present invention. The dose may be administered in a single or multiple doses per day. In terms of composition, the crude drug composition should be present between 0.01 to 80% by weight, preferably 0.5 to 50% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

In accordance with one aspect of the present invention, there provided a health functional food comprising the above described extract for the prevention or improvement of liver disease by protecting hepatic cell as an active ingredient in an amount effective to prevent and improve liver disease.

The crude drug composition of inventive health functional food is used in the form of pulverized form thereof, extracted form therefrom or dried extract form thereof.

The health functional food composition for preventing and improving liver diseases could contain about 0.01 to 95 w/w %, preferably 0.5 to 80 w/w % of the above crude drug composition of present invention based on the total weight of the composition.

The above described the crude drug composition therein can be added to food, additive or beverage for prevention and improvement of liver diseases. For the purpose of preventing and improving liver diseases, wherein, the amount of above described crude drug composition in food or beverage may generally range from about 0.1 to 15 w/w %, preferably 1 to 10 w/w % of total weight of food for the health food composition and 1 to 30 g, preferably 3 to 10 g on the ratio of 100 ml of the health beverage composition.

Providing that the health beverage composition of present invention contains above described crude drug composition as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose and etc.; disaccharide such as maltose, sucrose and etc.; conventional sugar such as dextrin, cyclodextrin; and sugar alcohol such as xylitol and erythritol, and etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 ml of present beverage composition.

The other components than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition.

Examples of addable food comprising aforementioned crude drug composition therein are various food, beverage, gum, vitamin complex, health improving food and the like.

It will be apparent to those skilled in the art that various modifications and variations can be made in the compositions, use and preparations of the present invention without departing from the spirit or scope of the invention.

Advantageous Effects

The combined herb composition according to the present invention shows potent inhibiting effect on the level of increased GOT, GPT, cholesterol, triglyceride, LDL-cholesterol as well as increasing effect on the level of reduced HDL-cholesterol together with preventing and treating liver cirrhosis and fatty liver.

The inventive compositions according to the present invention are useful in the prevention and treatment of the liver diseases and can be used as safe and efficient hepato-protective agent.

DESCRIPTION OF DRAWINGS

The above and other objects, features and other advantages of the present invention will more clearly understood from the following detailed description taken in conjunction with the accompanying drawings, in which.

BEST MODE

Figure 1:
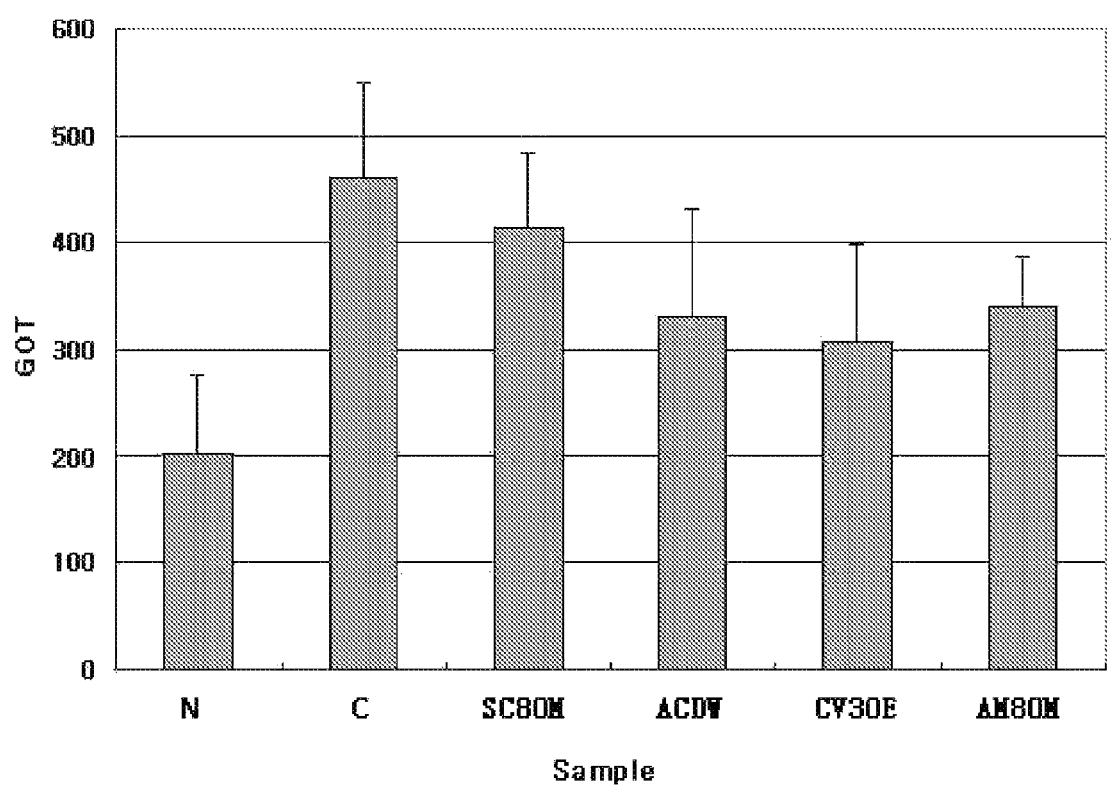
FIG. 1 shows the change of GOT level in the group treated with respective extract prepared in Comparative Example 1 in CCL4-induced rats.

The following Examples and Experimental Examples are intended to further illustrate the present invention without limiting its scope.

MODE FOR INVENTION

Comparative Example 1

Preparation of Respective Herb Extract (1)

1-1. The Crude Extract 1 of *Coriolus versicolor* (CV30E)

500 g of *Coriolus versicolor* purchased from Kyung-dong market located in Seoul were washed and 10 L of distilled water was added thereto. The solution was subjected to reflux extraction with distilled water at 100° C. twice at the 1st step. The extract obtained at the 1st step was filtered and concentrated at 105° C. to prepare 800 ml of concentrates. The concentrates were dried at 60° C. to obtain 62.0 g of dried crude extract of *Coriolus versicolor* (Yield: 12.4%).

1-2. The Crude Extract of *Astragalus Membranaceus Bunge* (AM80M)

800 g of *Astragalus membranaceus Bunge* purchased from Kyung-dong market located in Seoul were washed and 10 L of 70% ethanol solution was added thereto. The solution was subjected to reflux extraction at 100° C. twice at the 1st step. The extract obtained at the 1st step was filtered and concentrated at 105° C. to prepare 750 ml of the concentrates. The concentrates were dried at 60° C. to obtain 153.6 g of dried crude extract of *Astragalus membranaceus Bunge* (Yield: 19.2%).

1-3. The Crude Extract of *Schisandra chinensis* (SC80M)

500 g of *Schisandra chinensis* purchased from Kyung-dong market located in Seoul were washed and 10 L of 70% ethanol was added thereto. The solution was subjected to reflux extraction at 100° C. twice at the 1st step. The extract obtained at the 1st step was filtered and concentrated at 105° C. to prepare 900 ml of the concentrates. The concentrates were dried at 60° C. to obtain 183.0 g of dried crude extract of *Schisandra chinensis* (Yield: 36.6%).

1-4. The Crude Extract of *Artemisia capillaris* (ACDW)

500 g of *Artemisia capillaris* purchased from Kyung-dong market located in Seoul were washed and 10 L of distilled water was added thereto. The solution was subjected to reflux extraction at 100° C. twice at the 1st step. The extract obtained at the 1st step was filtered and concentrated at 105° C. to prepare 650 ml of the concentrates. The concentrates were dried at 60° C. to obtain 91.5 g of dried crude extract of *Artemisia capillaris* (Yield: 18.3%).

Comparative Example 2

Preparation of Respective Herb Extract (2)

2-1. The Lower Alcohol Insoluble Extract of *Coriolus versicolor* (CO)

1000 g of *Coriolus versicolor* purchased from Kyung-dong market located in Seoul were washed and 10 L of distilled water was added thereto. The solution was subjected to reflux extraction with distilled water at 100° C. for 2 hours twice at the 1st step. The extract obtained at the 1st step was filtered and concentrated at 105° C. to prepare 1000 ml of concentrates. 70% ethanol solution prepared by adding 95% ethanol to the concentrates were left alone in room temperature for 12 hours to separate supernatant layer and precipitate layer and the precipitates was dried at 60° C. to obtain 31.5 g of dried lower alcohol insoluble extract of *Coriolus versicolor* (Yield: 3.15%, designated as CO hereinafter).

2-2. The Crude Extract of *Astragalus Membranaceus Bunge* (AS)

1000 g of *Astragalus membranaceus Bunge* purchased from Kyung-dong market located in Seoul were washed and 10 L of 95% ethanol solution was added thereto. The solution was subjected to reflux extraction at 95° C. for 2 hours twice at the 1st step. The extract obtained at 1st step was filtered and concentrated at 105° C. for 3 hours to prepare 1000 ml of the concentrates. The concentrates were dried at 60° C. to obtain 80.3 g of dried crude extract of *Astragalus membranaceus Bunge* (Yield: 8.03%, designated as AS hereinafter).

2-3. The Non-Polar Solvent Soluble Extract of *Schisandra chinensis* (AR)

1000 g of *Schisandra chinensis* purchased from Kyung-dong market located in Seoul were washed and 10 L of 95% ethanol was added thereto. The solution was subjected to reflux extraction at 95° C. twice for 2 hours at the 1st step. The extract obtained at the 1st step was filtered and concentrated at 105° C. to prepare 1000 ml of the concentrates. Equivalent amount of hexane was added thereto to fractionate into water layer and hexane soluble layer and the hexane layer was collected obtain the hexane soluble extract of *Schisandra chinensis* (Yield: 1.21%, designated as AR hereinafter).

2-4. The Lower Alcohol Insoluble Extract of *Artemisia capillaris* (SC)

1000 g of *Artemisia capillaris* purchased from Kyung-dong market located in Seoul were washed and 10 L of distilled water was added thereto. The solution was subjected to reflux extraction at 100° C. for 2 hours twice at the 1st step. The extract obtained at the 1st step was filtered and concentrated at 105° C. to prepare 1000 ml of the concentrates. 70% ethanol solution prepared by adding 95% ethanol to the concentrates were left alone in room temperature for 12 hours to separate supernatant layer and precipitate layer and the precipitates was dried at 60° C. to obtain 119.7 g of dried lower alcohol insoluble extract of *Artemisia capillaris* (Yield: 11.97%, designated as SC hereinafter).

Example 1

Preparation of Combined Inventive Formulations (1)

1-1. Preparation of Inventive H1

Each extract of *Coriolus versicolor* and *Astragalus membranaceus Bunge* prepared in Comparative Example 1 was mixed with the weight ratio of 1:1 to prepare inventive combined formulation (designated as H1 hereinafter).

1-2. Preparation of Inventive H2

Each extract of *Coriolus versicolor, Astragalus membranaceus Bunge* and *Schisandra chinensis* prepared in Comparative Example 1 was mixed with the weight ratio of 1:1:1 to prepare inventive combined formulation (designated as H2 hereinafter).

1-3. Preparation of Inventive H3

Each extract of *Coriolus versicolor, Astragalus membranaceus Bunge* and *Artemisia capillaris* prepared in Comparative Example 1 was mixed with the weight ratio of 1:1:1 to prepare inventive combined formulation (designated as H3 hereinafter).

1-4. Preparation of Inventive H4

Each extract of *Coriolus versicolor, Astragalus membranaceus Bunge, Schisandra chinensis* and *Artemisia capillaris* prepared in Comparative Example 1 was mixed with the weight ratio of 1:1:1:1 to prepare inventive combined formulation (designated as H4 hereinafter).

Example 2

Preparation of Combined Inventive Formulations (2)

2-1. Preparation of Inventive HF1

Each extract of *Coriolus versicolor* and *Astragalus membranaceus Bunge* prepared in Comparative Example 2 was mixed with the weight ratio of 1:1 to prepare inventive combined formulation (designated as HF-1 hereinafter).

2-2. Preparation of Inventive HF2

Each extract of *Coriolus versicolor, Astragalus membranaceus Bunge* and *Schisandra chinensis* prepared in Comparative Example 2 was mixed with the weight ratio of 1:1:1 to prepare inventive combined formulation (designated as HF2 hereinafter).

2-3. Preparation of Inventive HF3

Each extract of *Coriolus versicolor, Astragalus membranaceus Bunge* and *Artemisia capillaris* prepared in Comparative Example 2 was mixed with the weight ratio of 1:1:1 to prepare inventive combined formulation (designated as HF3 hereinafter).

2-4. Preparation of Inventive HF4

Each extract of *Coriolus versicolor*, *Astragalus membranaceus Bunge*, *Schisandra chinensis* and *Artemisia capillaris* prepared in Comparative Example 2 was mixed with the weight ratio of 1:1:1:1 to prepare inventive combined formulation (designated as HF4 hereinafter).

Experimental Example 1

Effect on CCl4-Induced Chronic Liver Injury in Rat Model

In order to investigate the inhibitory effect of the inventive combined extract obtained in Example 1 on liver injury comparing with Comparative Example 1, following experiment was performed in the procedure.

1-1. Reagent and Experimental Animals

CCl4 (Sigma Co.), Olive oil (Sigma Co.), Alanine Amino Transferase (ALT, GPT, Stanbio Co.) and aspartate amino transferase (AST, GOT, Stanbio Co.) was purchased from commercial company to use in experimental.

Male Sprague-Dawley rats weighing about 200 g (Daehan Biolink Co. Ltd., Korea) were used in the experiment and were allowed to freely access to feed (Harlan, teklan, USA) and drinking water. All animals were maintained in a controlled environment with temperatures at 21° C.-24° C. and humidity at 60%-80% with 12 hours of light and dark cycles for at least one week prior to use. The mean weight of mice in each group was optimized according to each group and 10 mice were used in each group.

1-2. The Effect of Respective Herb on CCl4-Induced Chronic Liver Injury

For the estimation of the effect on liver injury, the normal group was treated with only saline solution. The mixed solution with olive oil and CCl4 (1:3) was administrated into each experimental rat with a dosage of 1.0 ml/kg for three days, intraperitoneally to induce acute hepatotoxicity to use as a control group. One hour after the inducement, various concentrations of extract disclosed in Comparative Example 1 suspended with saline solution, were orally administrated into the rats with a dosage of 1.0 ml/kg for three days as test groups and the equivalent amount of saline solution was only treated thereto as a negative control. 18 hours after the induction, the blood sample was pooled from suborbital vena and centrifuged for 20 mins at 3000 rpm. Each GOT and GPT level of each sample was determined using by BT2000+ apparatus (SEAC Co.).

Figure 2:
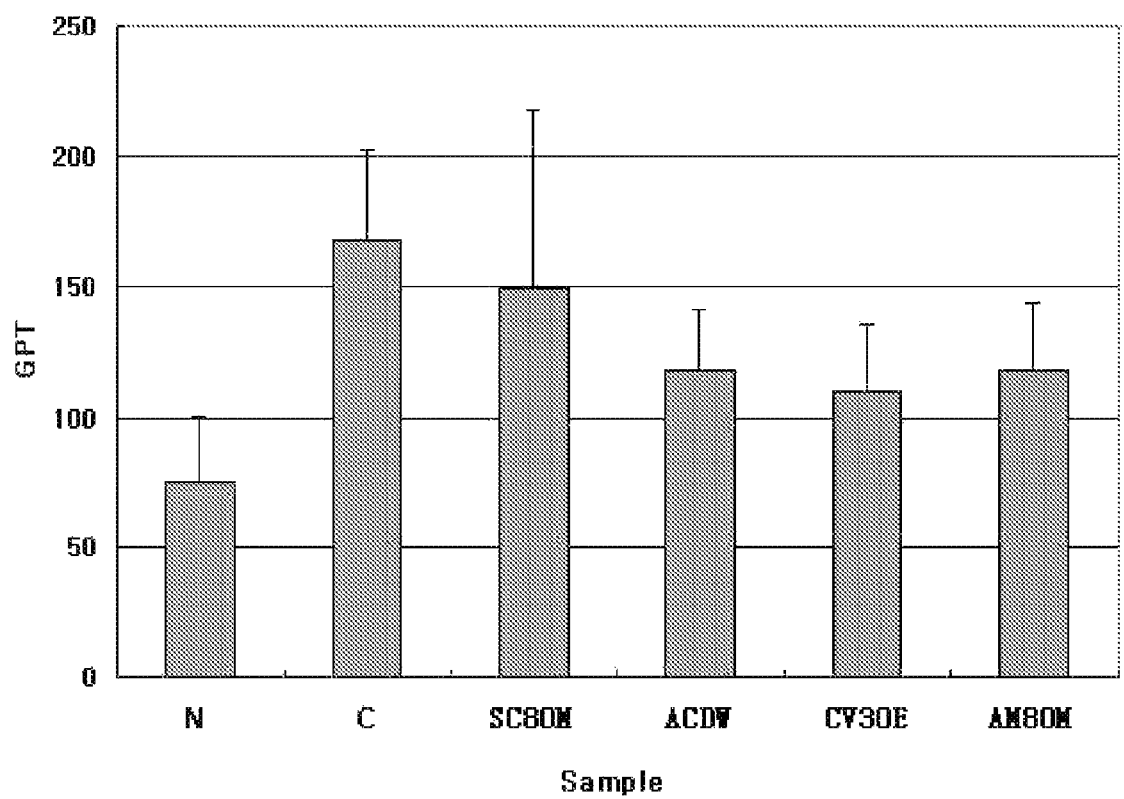
FIG. 2 shows the change of GPT level in the group treated with respective extract prepared in Comparative Example 1 in CCL4-induced rats.

As can be seen in FIGS. 1 and 2, the normal group treated with only saline solution showed about 200 U/l of GOT level and 74 U/l of GPT level whereas the control group treated with the mixed solution with olive oil and CCl4 (1:1) showed about 461 U/l of GOT level and 168 U/l of GPT level. However, the test groups treated with each herb extract showed hepato-protective activity in the order of *Coriolus versicolor*, *Schisandra chinensis*, *Astragalus membranaceus Bunge*, and *Artemisia capillarys* (See FIGS. 1 and 2).

Accordingly, it is confirmed that the inventive extract of the present invention is effective in alleviating liver function.

1-3. The Effect of Combined Formulations on CCl4-Induced Chronic Liver Injury

For the estimation of the effect on liver injury, the normal group was treated with only saline solution. The mixed solution with olive oil and CCl4(1:1) was administrated into each experimental rat with a dosage of 1.0 ml/kg for three days, intraperitoneally to induce acute hepatotoxicity to use as a control group. One hour after the inducement, various concentrations of inventive combined extract disclosed in Example 1, i.e., H1, H2, H3 and H4, suspended with saline solution, were orally administrated into the rats with the dose of 1 g/60 kg for three days as test groups and the equivalent amount of saline solution was only treated thereto as a negative control. 18 hours after the induction, the blood sample was pooled from suborbital vena and centrifuged for 20 mins at 3000 rpm. Each GOT and GPT level of each sample was determined using by BT2000+ apparatus (SEAC Co.).

Figure 3:
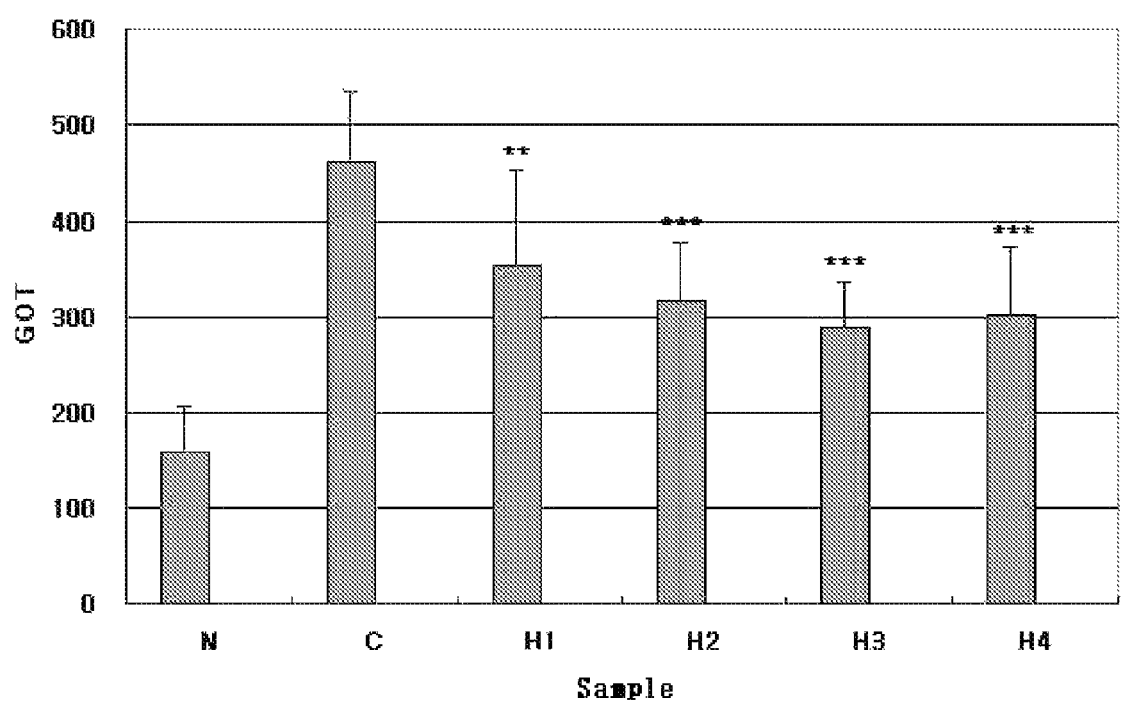
FIG. 3 shows the effect on the change of GOT level of the combined extract prepared in Example 1 in CCL4-induced hepatic injury prevention model.
Figure 4:
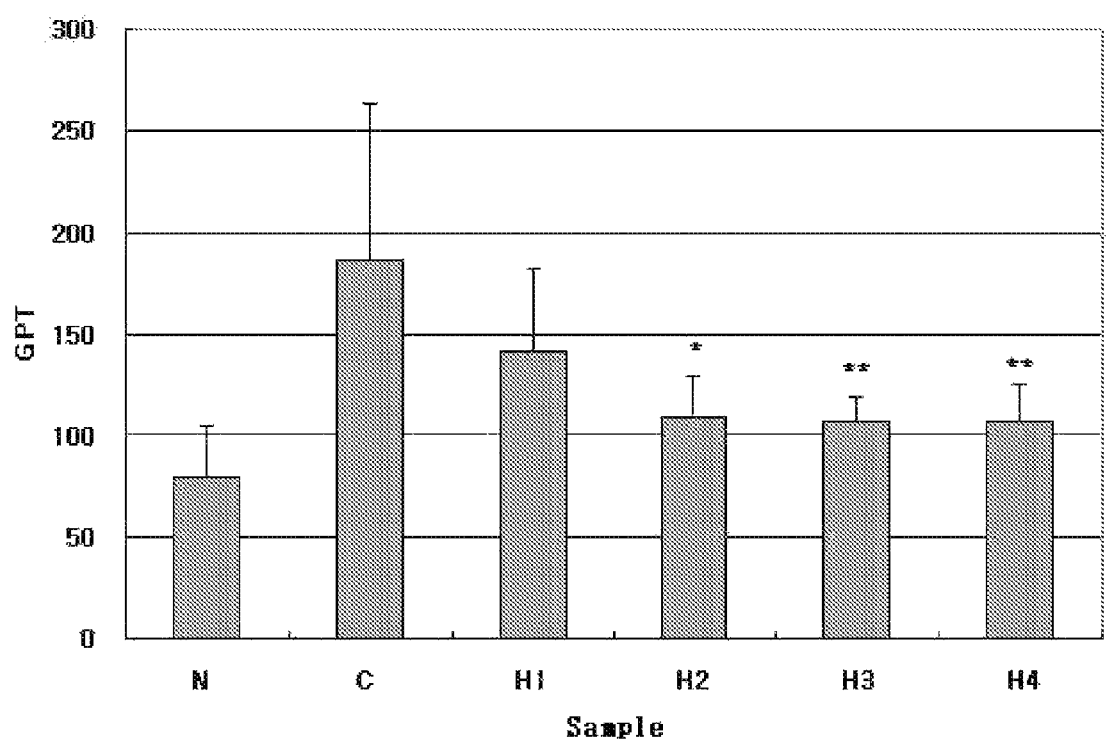
FIG. 4 shows the effect on the change of GPT level of the combined extract prepared in Example 1 in CCL4-induced hepatic injury prevention model.

As can be seen in FIGS. 3 and 4, the control group treated with the mixed solution with olive oil and CCl4(1:1) only saline solution showed about 462 U/l of GOT level and 186 U/l of GPT level whereas the test group treated with H1 showed about 355 U/l of GOT level and 142.1 U/l of GPT level. The levels of GOT and GPT in test group treated with H2 were similar to those in test group treated with H3, which showed more potent hepatoprotective activity than the group treated with H1. However, the test groups treated with H4 showed most potent hepato-protective activity among them (See FIGS. 3 and 4).

Accordingly, it is confirmed that the inventive combined extract of the present invention is effective in treating and preventing liver disease.

1-4. The Effect of Combined Formulations on CCl4-Induced Chronic Liver Injury

For the estimation of the alleviation effect on liver injury, the normal group was treated with only saline solution for four days. The mixed solution with olive oil and CCl4(1:1) was administrated into each experimental rat with a dosage of 1.0 ml/kg for three days, intraperitoneally to induce acute hepatotoxicity to use as a control group. One hour after the inducement, various concentrations of inventive combined extract disclosed in Example 1, i.e., H1, H2, H3 and H4, suspended with saline solution, were orally administrated into the rats with the dose of 1 g/60 kg for four days as test groups and the equivalent amount of saline solution was only treated thereto as a negative control. At the final test day, 1.5 ml of blood from the anesthetized experimental animals was pooled and fixed with reperfusion. The blood sample was centrifuged for 20 mins at 3000 rpm, and each GOT and GPT level of each sample was determined using by CH100+ apparatus (SEAC Co.).

Figure 5:
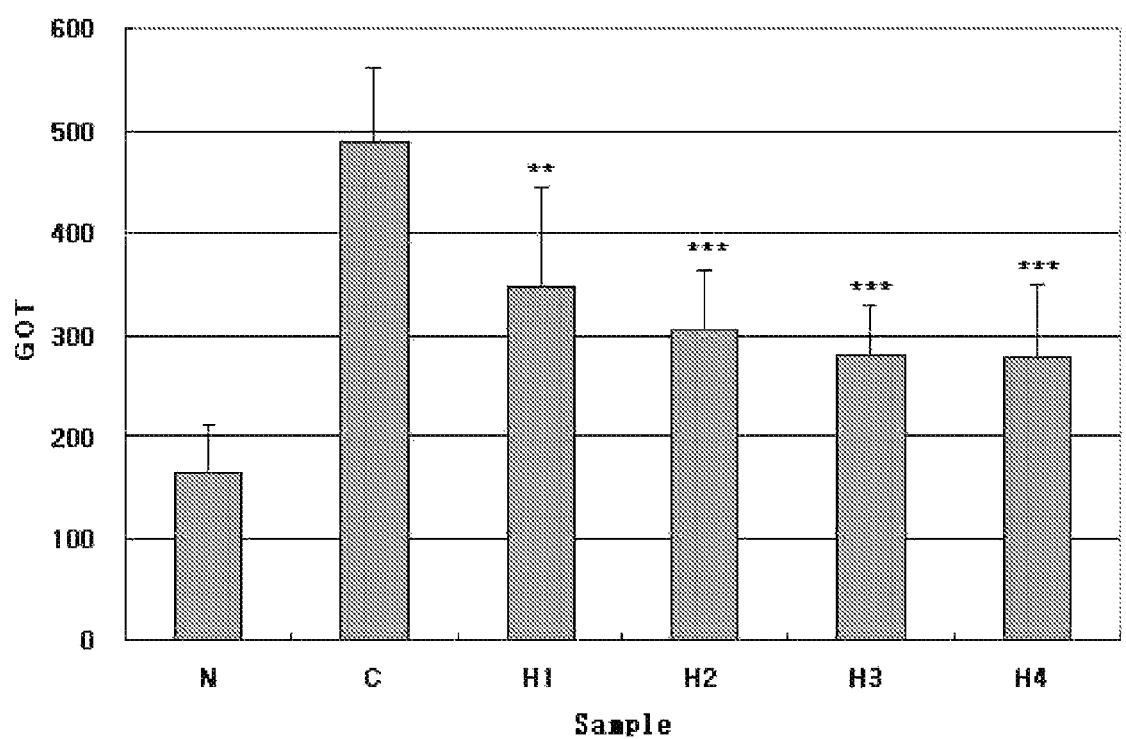
FIG. 5 shows the effect on the change of GOT level of the combined extract prepared in Example 1 in CCL4-induced hepatic injury treatment model.
Figure 6:
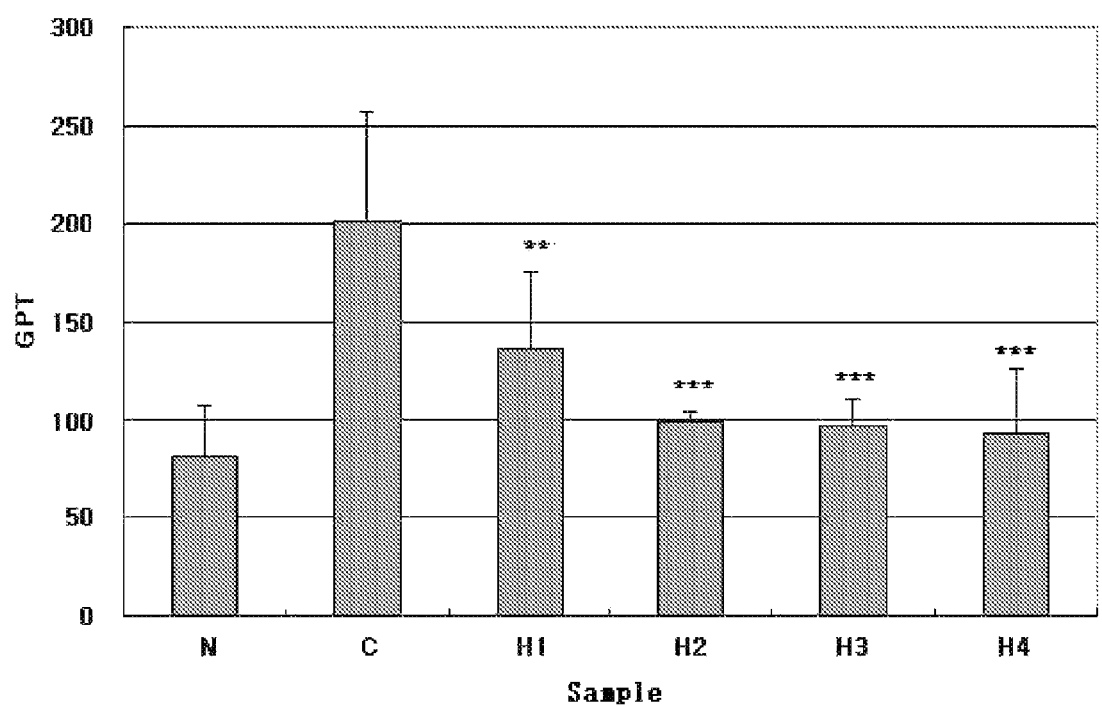
FIG. 6 shows the effect on the change of GPT level of the combined extract prepared in Example 1 in CCL4-induced hepatic injury treatment model.

As can be seen in FIGS. 5 and 6, the control group treated with the mixed solution with olive oil and CCl4(1:1) only saline solution showed about 488 U/l of GOT level and 201.4 U/l of GPT level whereas the groups treated H1, H2 and H3 showed about 347.6, 304.1 and 107.9 U/l of GOT level and 136.4, 99.2 and 97.3 U/l of GPT level respectively. The levels of GOT and GPT in test group treated with H4 were similar to those in test group treated with H2 and H3, which showed a rather potent treating activity than the groups treated with H2 and H3 (See FIGS. 5 and 6).

Experimental Example 2

Effect on Collagen Distribution and Inhibition of GOT and GPT Level in Rat Model In order to investigate the improving effect of the inventive extract obtained in Example 1 on liver cirrhosis, following experiment was performed in the procedure.

2-1. Reagent and Experimental Animals

DMN (Dimethylnitrosoamine, Sigma Co.), Alanine Amino Transferase (ALT, GPT, Stanbio Co.) and aspartate amino transferase (AST, GOT, Stanbio Co.) was purchased from commercial company to use in experimental.

Wister rats weighing about 270 g were used in the experiment and were allowed to access to feed (Harlan, teklan, USA) and drinking water. All animals were maintained in a controlled environment with temperatures at 21° C.-24° C. and humidity at 60%-80% with 12 hours of light and dark cycles for at least one week prior to use.

2-2. The Effect on Collagen Distribution and Inhibitory Effect on GOT and GPT

For the estimation of the effect on liver cirrhosis, 1% DMN (Dimethylnitrosamine) was administrated into each experimental rat with a dosage of 40 mg/kg/day for three days intraperitoneally to induce liver cirrhosis. The inventive combined extract prepared in Example 1 suspended in saline solution were orally administrated into the rats for two weeks in a amount of 1 g/60 kg of weight as test groups and the equivalent amount of saline solution was only treated thereto as a negative control. At the final test day, 1.5 ml of blood from the anesthetized experimental animals was pooled and fixed with reperfusion. The blood sample was centrifuged for 20 mins at 3000 rpm, and each GOT and GPT level of each sample was determined using by CH100+ apparatus (SEAC Co.).

To examine the collagen distribution in liver tissue, Masson trichrome staining method which stains only collagen part and the isolated liver tissue was embedded with automatic tissue analyzer (Citadel 2000, Shandon Co.) and sliced into pieces at the width of 4 micrometer using by tissue microtome (LEICA RM2145). Each 5 lesion for each tissue was selected and fibrinous ratio of the lesion was determined by image analysis system. The mean values of the ratio was calculated and transformed into the collagen amount.

Figure 7:
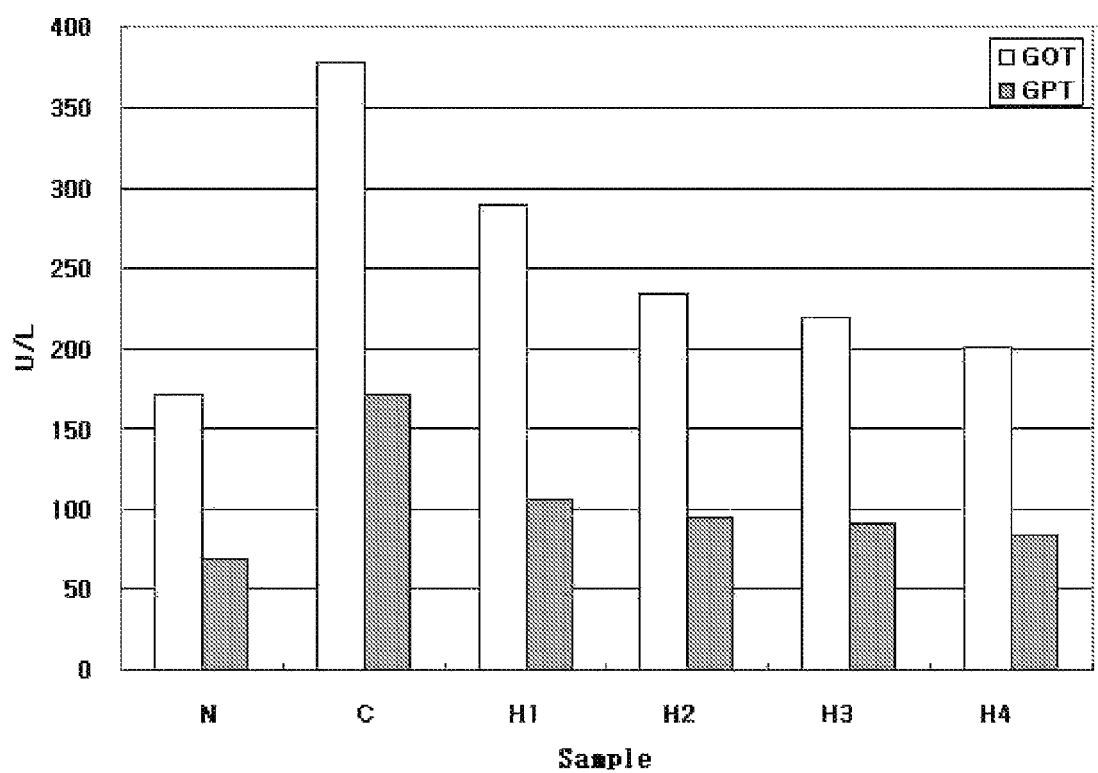
FIG. 7 represents the change of GOT and GPT level in DMN-induced liver cirrhosis model.

As can be seen in FIG. 7, the groups treated with inventive extract obtained in Example 1 significantly inhibited GOT and GPT level of liver injury rat model. The groups treated with H2 and H3 showed more potent inhibitory activity than that treated with H1 and the group treated with H4 showed most potent activity among test groups (significance: $p<0.0001$, See FIG. 7).

Figure 8:
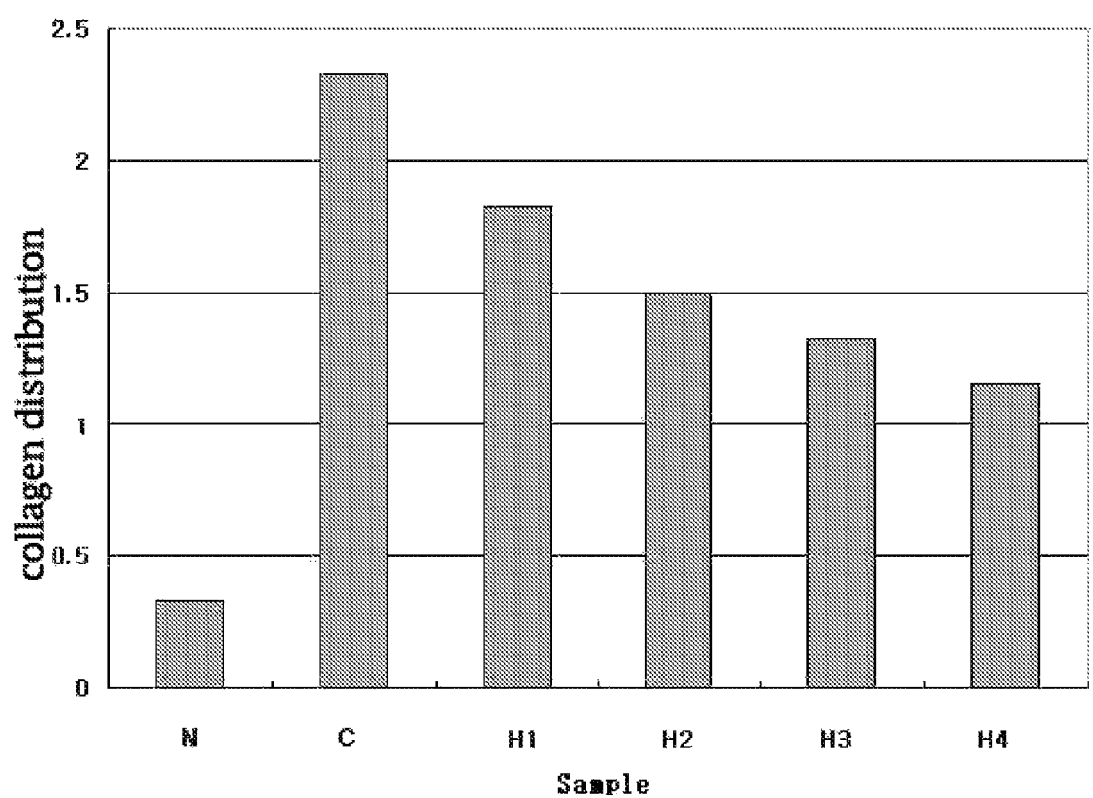
FIG. 8 represents the effect on the collagen distribution in DMN-induced liver cirrhosis model.

Furthermore, the collagen amount of the groups treated with inventive extract H1, H2, H3 and H4 obtained in Example 1 showed 1.83, 1.5, 1.33 and 1.66 respectively while those of control group and normal groups showed 2.44 and 1.33 respectively (See FIG. 8).

Accordingly, it is confirmed that the inventive extract of the present invention is effective in inhibiting the progress of liver fibrosis significantly.

Experimental Example 3

Effect on Alcohol-Induced Fatty Liver in Rat Model

In order to investigate the inhibitory effect of the inventive combined extract obtained in Example 2 on fatty liver comparing with Comparative Example 2, following experiment was performed in the procedure.

3-1. Experimental Animals & Pretreatment

Male Sprague-Dawley rats weighing about 200 g (Samtaco Co. Ltd., Korea) were used in the experiment and were allowed to freely access to feed and drinking water. All animals were maintained in a controlled environment with temperatures at 22±2° C. and humidity at 60±5% with 12 hours of light and dark cycles for at least one week prior to use. The mean weight of mice in each group was optimized according to each group and 10 mice were used in each group.

3-2. Pretreatment

To induce fatty liver, animal feed (AIN 76 containing 1% cholesterol, Feedlab Co. Ltd.) was orally administrated into the experimental rats for 21 days. Additionally, 35% ethanol has been orally administrated to the experimental rats in an amount of 10 mg/kg since eight days after the feed administration to use as a control group and the extract prepared in Comparative Example 2 and Example 2 was orally administrated into the rats 10 days after the feed administration with a dose of 50 mg/kg. 21 days after the oral administration, the experimental animals were anaesthetized with ether to use in following experiments.

3-3. The Effect on the GOT and GPT Level in Fatty Liver

For determining the effect on the change of blood GOT and GPT concentration by the inventive combined extract obtained in Example 2 in fatty liver, following test was performed by the procedure disclosed in literature (Bergmeyer H U, Scheibe P, Wahlefeld A W: optimization of methods for asparate aminotransferase and alanine aminotransferase. Clin Chem 24:58, 1978).

After performing the method similar to the method disclosed in 3-2, the blood from the anesthetized experimental animals was pooled. The blood sample was centrifuged for 20 mins at 4,550×g, and each GOT and GPT level in the serum were determined using by BT2000+ apparatus (SEAC Co.).

Figure 9:
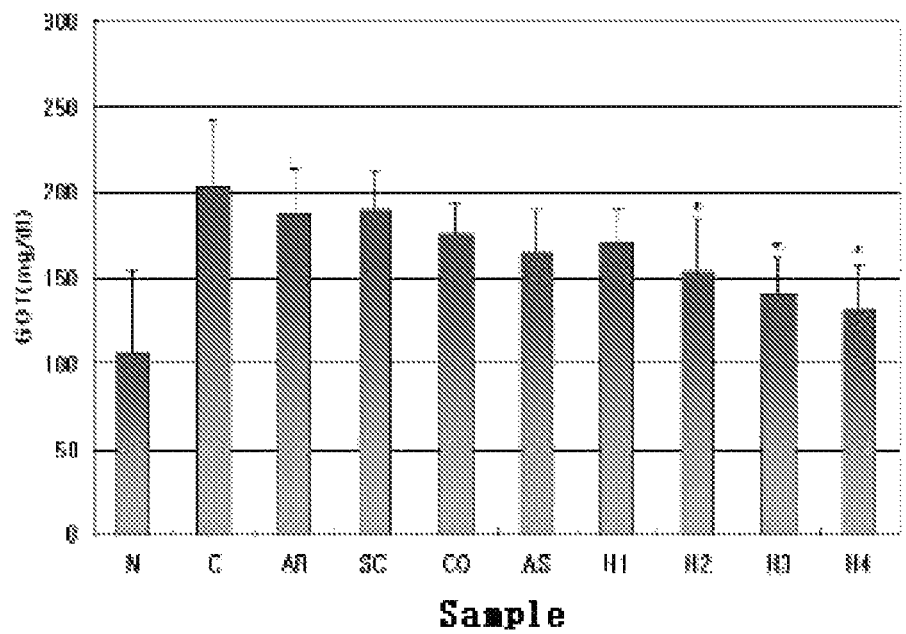
FIG. 9 shows the change of GOT and GPT level in the group treated with respective extract prepared in Comparative Example 2 and Example 2 in alcohol-induced fatty liver of rats.
Figure 9:
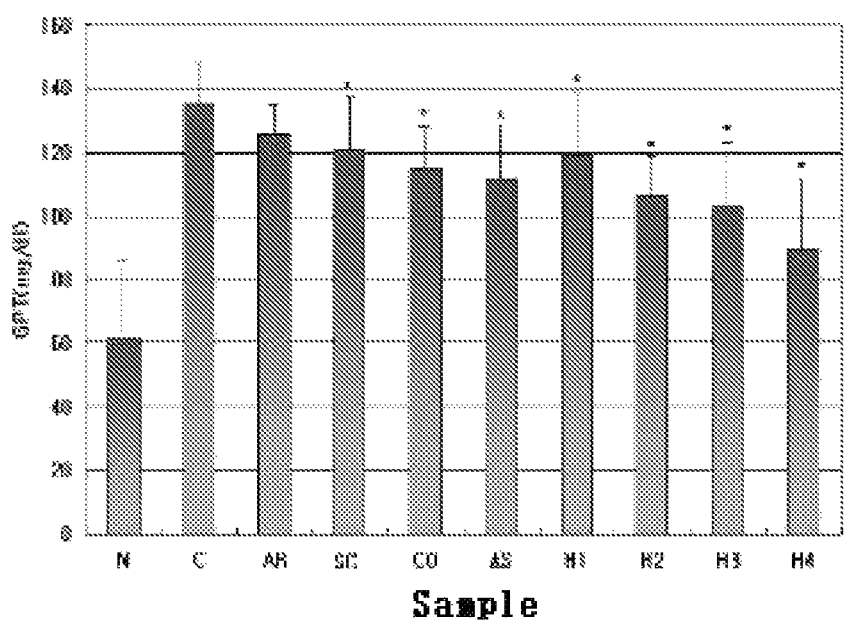

As can be seen in FIG. 9, the test group treated with respective herb prepared in Comparative Example 2 could not reduce significantly the increased GOT and GPT level induced by 1% cholesterol and 35% alcohol while that treated with combined herbs prepared in Example 2 significantly reduced the level of GOT and GPT, inter alia, the group treated with HF4 (GOT: 131.2 mg/dl, GPT: 89.6 mg/dl) showed most potent reducing effect on the increased level of GOT and GPT in alcohol-induced fatty liver model among them (See, FIG. 9).

3-4. The Effect on the Blood Lipid Concentration in Fatty Liver

For determining the effect on the change of blood lipid concentration in fatty liver, following test was performed by the procedure disclosed in literature (Trinder, P. Determination of glucose in blood using glucose oxidase with an alternative oxygen acceptor. Ann Clin Bio Chem. 6; 24-27, 1969.)

After performing the method similar to the method disclosed in 3-2, the blood from the anesthetized experimental animals was pooled. The blood sample was centrifuged for 20 mins at 4,550×g, and each cholesterol, triglyceride, HDL and LDL level in the serum were determined using by BT2000+ apparatus (SEAC Co.)

The Result of Level of Cholesterol

Figure 10:
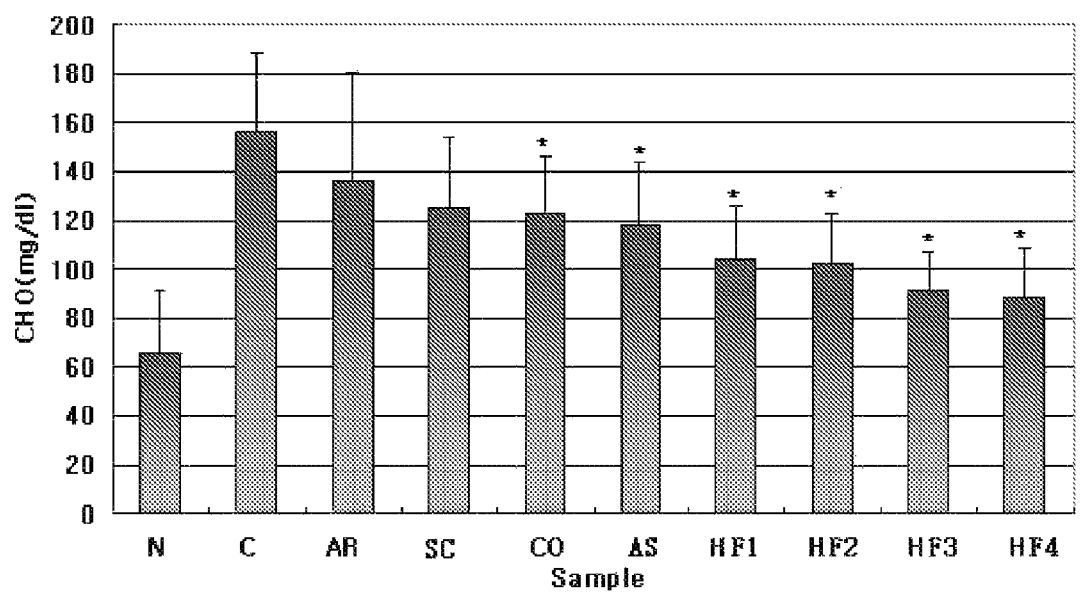
FIG. 10 shows the change of blood cholesterol level in the group treated with respective extract prepared in Comparative Example 2 and Example 2 in alcohol-induced fatty liver of rats.

As can be seen in FIG. 10, the control group treated with 1% cholesterol and 35% alcohol (158.1 mg/dl) showed 2-folds increased level of blood cholesterol comparing with normal group treated with none (65.6 mg/dl) whereas the groups treated with extracts prepared in Comparative Example 2 and Example 2 showed significant reducing effect on the increased cholesterol, inter alia, the group treated with HF3 (91.5 mg/dl) and HF4 (88.2 mg/dl) showed most potent reducing effect on the increased level of blood cholesterol in alcohol-induced fatty liver model among them (See, FIG. 10).

The Result of Level of Triglyceride

Figure 11:
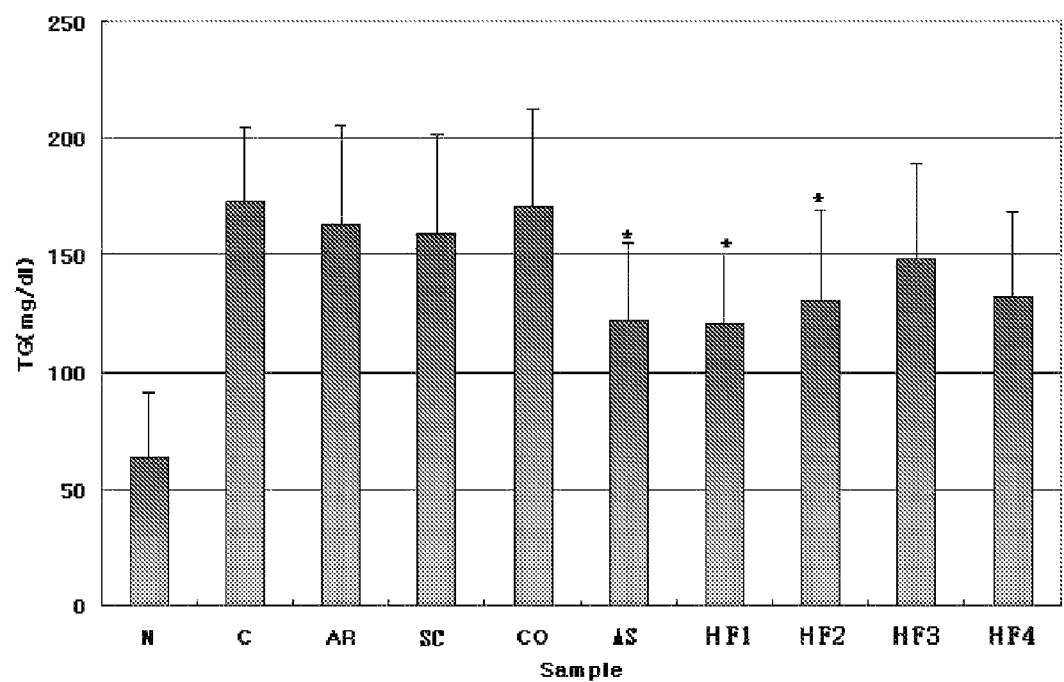
FIG. 11 shows the effect on the change of blood triglyceride level of the extract prepared in Comparative Example 2 and Example 2 in alcohol-induced fatty liver of rats.

As can be seen in FIG. 11, the control group treated with 1% cholesterol and 35% alcohol (173.2 mg/dl) showed 3-folds increased level of blood triglyceride comparing with normal group treated with none (63.6 mg/dl) whereas the groups treated with extracts prepared in Comparative Example 2 and Example 2 showed significant reducing effect on the increased triglyceride, inter alia, the group treated with HF1 (120.2 mg/dl) showed most potent reducing effect on the increased level of blood triglyceride in alcohol-induced fatty liver model among them (See, FIG. 11).

The Result of Level of HDL-Cholesterol & LDL-Cholesterol

Figure 12:
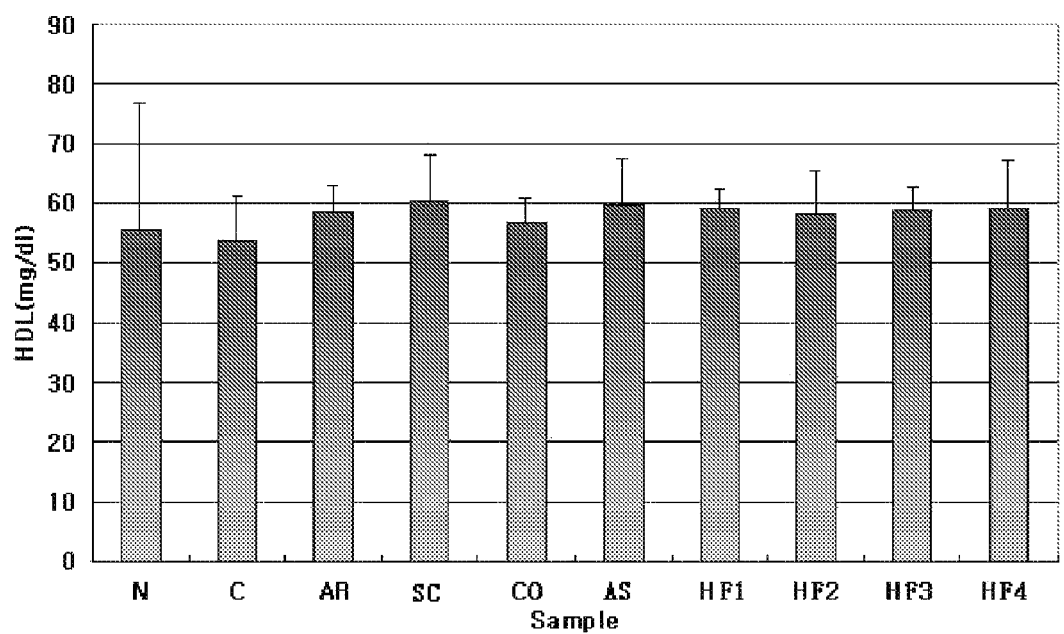
FIG. 12 shows the effect on the change of blood HDL-cholesterol level of the extract prepared in Comparative Example 2 and Example 2 in alcohol-induced fatty liver of rats.

As can be seen in FIG. 12, the control group treated with 1% cholesterol and 35% alcohol (53.8 mg/dl) showed decreased level of blood HDL-cholesterol comparing with normal group treated with none (55.4 mg/dl) whereas the groups treated with extracts prepared in Comparative Example 2 and Example 2 showed significant increasing effect on the reduced HDL (See, FIG. 12).

Figure 13:
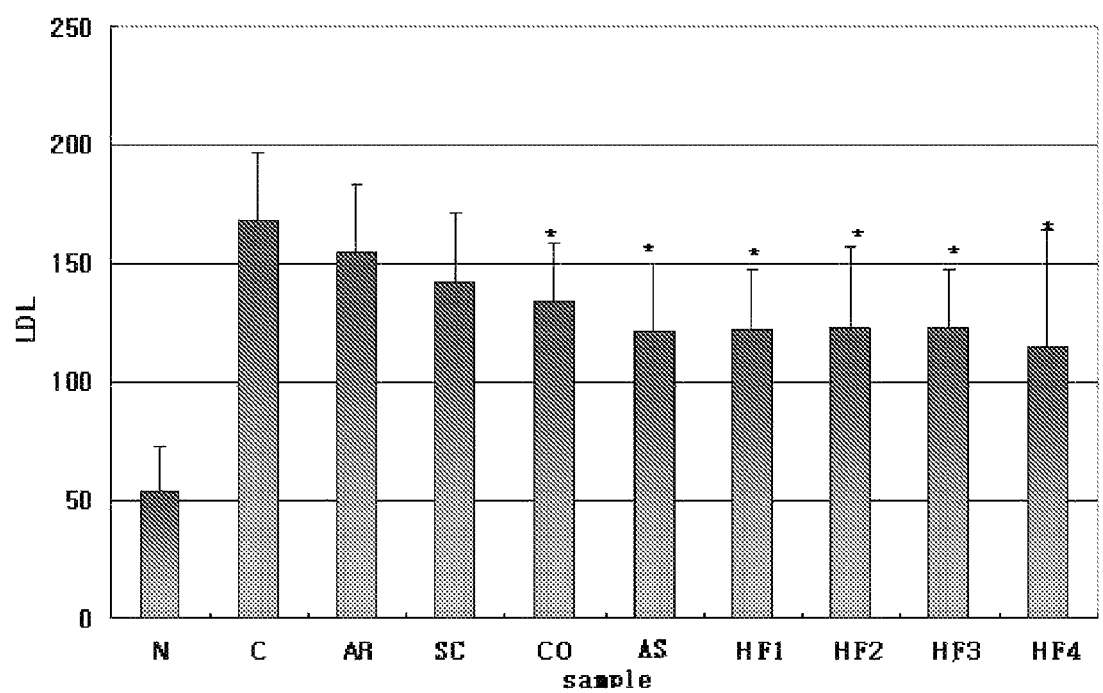
FIG. 13 shows the effect on the change of blood LDL-cholesterol level of the extract prepared in Comparative Example 2 and Example 2 in alcohol-induced fatty liver of rats.

As can be seen in FIG. 13, the control group treated with 1% cholesterol and 35% alcohol (168.7 mg/dl) showed more than 3 folds increased level of blood LDL-cholesterol comparing with normal group treated with none (53.2 mg/dl) whereas the groups treated with extracts prepared in Comparative Example 2 and Example 2 showed significant reducing effect on the increased LDL, similarly to the result in FIG. 10, inter alia, the group treated with HF4 (114.8 mg/dl) showed most potent reducing effect on the increased level of blood LDL in alcohol-induced fatty liver model among them (See, FIG. 13).

Through the above-described results, it has been confirmed that the extracts prepared in Comparative Example 2 and Example 2 showed potent reducing effect on the level of increased cholesterol, triglyceride, LDL-cholesterol as well as increasing effect on the level of reduced HDL-cholesterol resulting in inhibiting the lipid accumulation in the serum.

Experimental Example 4

Determination of Lipid Content Change in Liver

In order to investigate the inhibitory effect of the inventive combined extract obtained in Example 2 on the lipid content in fatty liver comparing with Comparative Example 2, following experiment was performed according the method disclosed in the literature (Zlatkis, A and Zak, B. Study of a new cholesterol reagent. Anal. biochem, 29, 143-148, 1969)

After performing the method similar to the method disclosed in 3-2, the liver was delivered from the experimental rats and 2 ml of saline solution was added to 1 g of liver section. The tissue was grinded with homogenizer and 3 ml of CM mixture solvent (chloroform:Methanol=2:1) was added thereto. The above-described steps were repeated three times and the suspension was centrifuged at the speed of 3000 rpm for 10 minutes. The chloroform layer was recovered and the solvent was removed by nitrogen gas. Triton X-100 comprising chloroform was added thereto to prevent lipid rancidity and the remaining chloroform was removed by nitrogen gas again. The level of total cholesterol and triglyceride was determined by using by BT2000+ apparatus (SEAC Co.).

The Result of Level of Total Cholesterol

Figure 14:
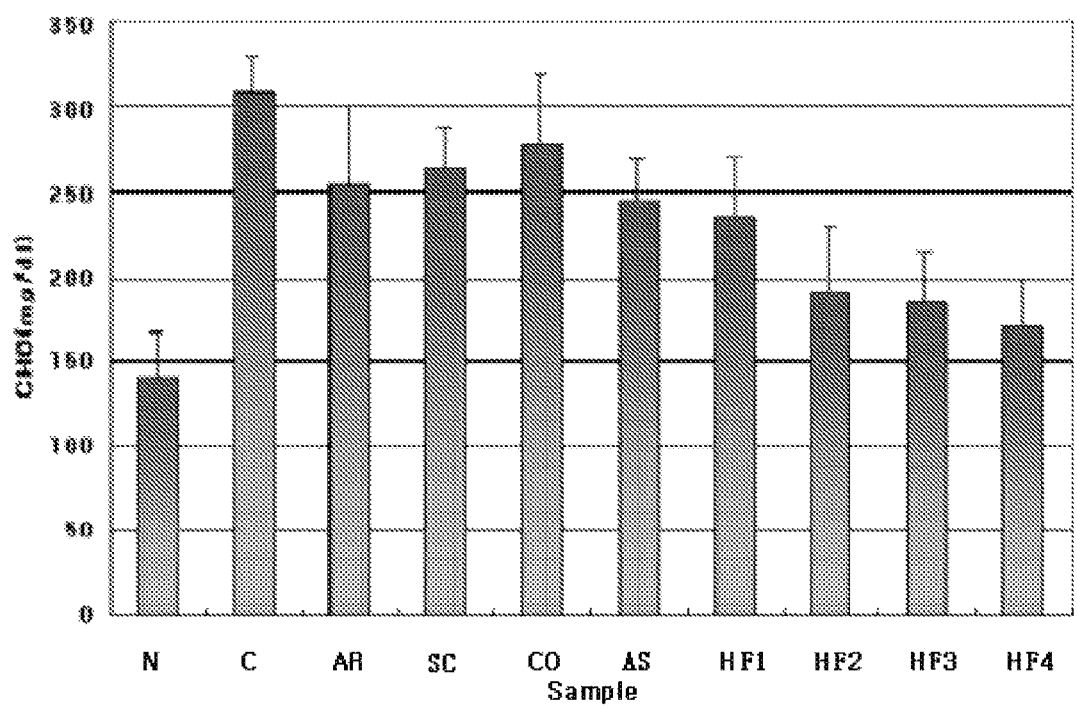
FIG. 14 shows the effect on the change of hepatic cholesterol level of the extract prepared in Comparative Example 2 and Example 2 in alcohol-induced fatty liver of rats.

As can be seen in FIG. 14, the control group treated with 1% cholesterol and 35% alcohol (308.43 mg/dl) showed more than 2 folds increased level of blood total cholesterol comparing with normal group treated with none (139.75 mg/dl) whereas the groups treated with extracts prepared in Comparative Example 2 and Example 2 showed significant reducing effect on the increased total cholesterol, inter alia, the groups treated with HF2, HF3 and HF4(HF2: 189.87 mg/dl, HF3: 185.54 mg/dl, HF4: 169.85 mg/dl) showed potent reducing effect on the increased level of blood total cholesterol among them (See, FIG. 14).

The Result of Level of Total Triglyceride

Figure 15:
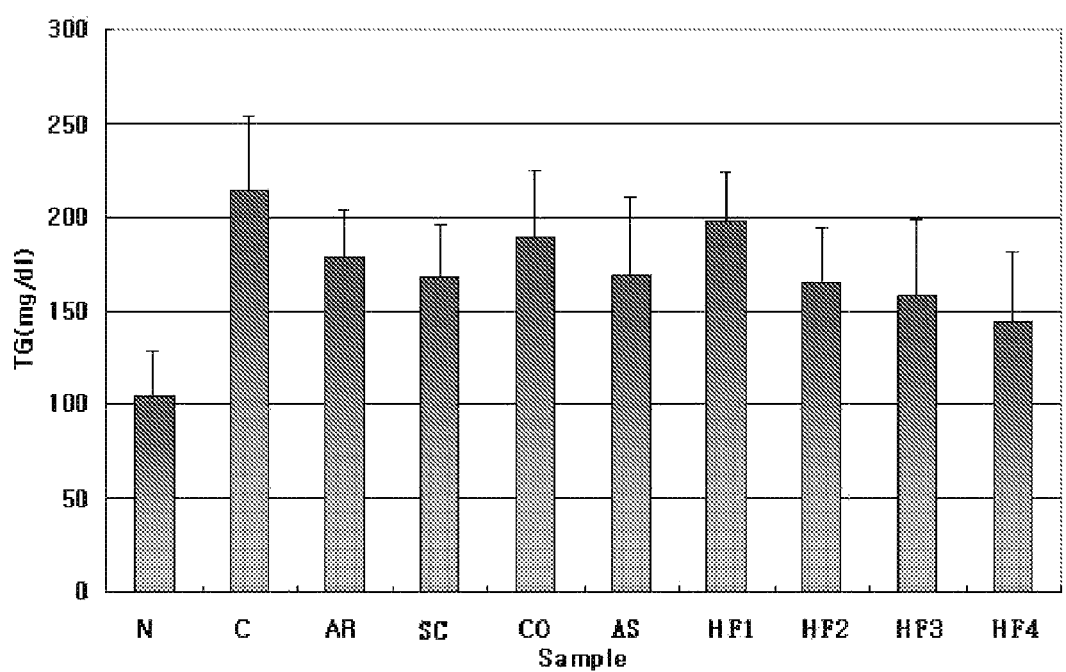
FIG. 15 shows the effect on the change of hepatic triglyceride level of the extract prepared in Comparative Example 2 and Example 2 in alcohol-induced fatty liver of rats.

As can be seen in FIG. 15, the control group treated with 1% cholesterol and 35% alcohol (173.2 mg/dl) showed more than 2 folds increased level of blood total triglyceride comparing with normal group treated with none (63.6 mg/dl) whereas the groups treated with extracts prepared in Comparative Example 2 and Example 2 showed significant reducing effect on the increased total triglyceride, similarly to the result in FIG. 14, inter alia, the groups treated with HF2, HF3, and HF4 (HF2: 165.5 mg/dl, HF3: 158.1 mg/dl and HF4: 143.0 mg/dl) showed potent reducing effect on the increased level of blood triglyceride among them (See, FIG. 15).

Accordingly, it has been confirmed that the groups treated with extracts prepared in Comparative Example 2 and Example 2 showed potent reducing effect on the increased level of blood cholesterol and triglyceride in liver among them.

Experimental Example 5

Determination of the Change of Liver Tissue

In order to investigate the effect of the inventive combined extract (HF2, HF3 and HF4) obtained in Example 2, on the morphological change of liver tissue comparing with Comparative Example, following experiment was performed according the method disclosed in the literature (Hematoxylin and Eosin (H&E) staining, http://www.protocol-online.org).

After performing the method similar to the method disclosed in 3-2, the liver was delivered and the liver tissue was fixed with 10% formalin to stain by H&E staining method (Hematoxylin and Eosin staining, http://www.protocol-oline.org).

The Result of the Change of Liver Morphology

Figure 16:
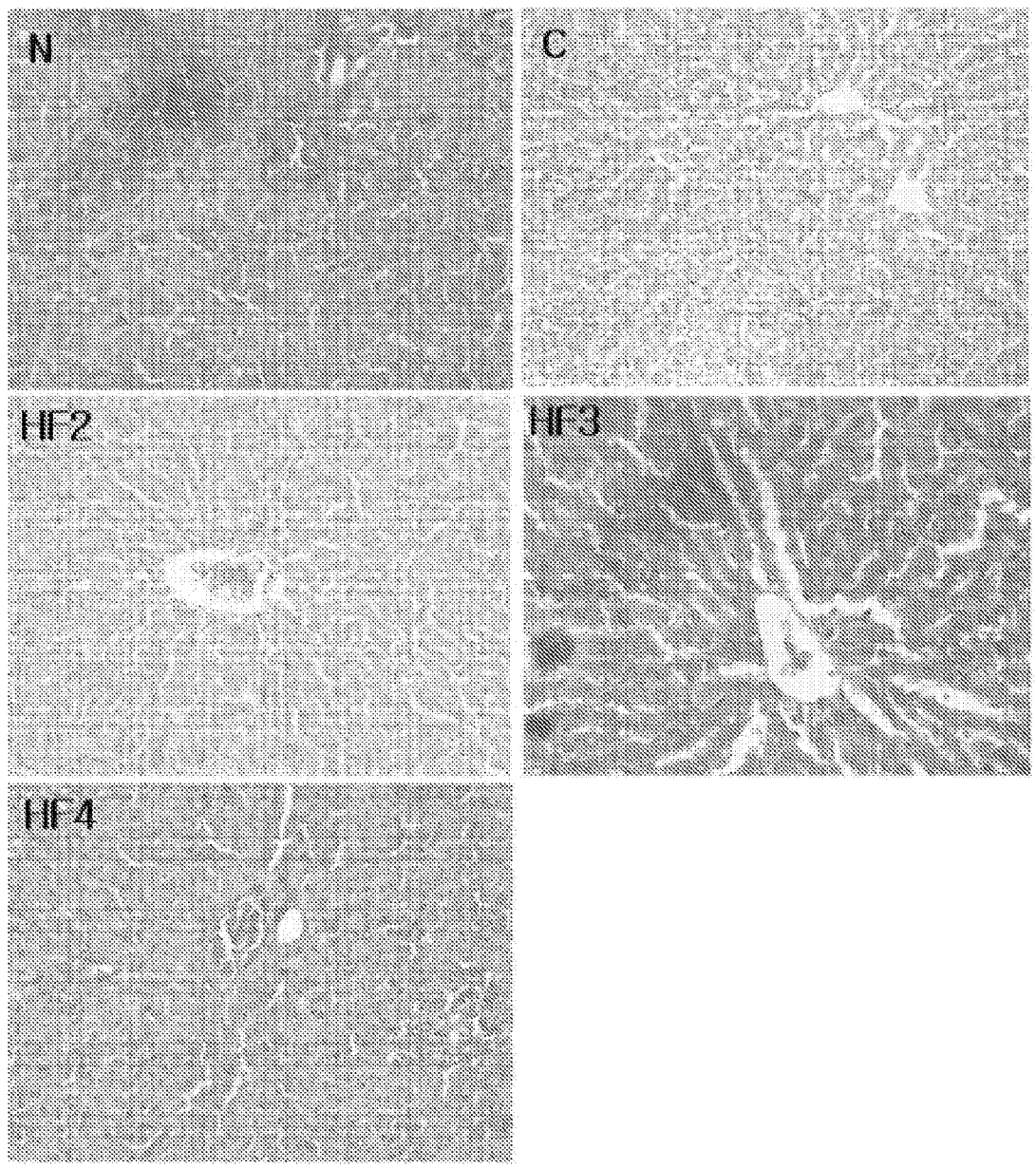
FIG. 16 represents the effect on the morphological change of liver tissue of the combined extract prepared in Example 2 in alcohol-induced fatty liver of rats.

As can be seen in FIG. 16, the control group treated with 1% cholesterol and 35% alcohol showed increased number of lipid droplets neighboring the blood vessel and abnormal morphology in the shape of hepatic cell comparing with normal group treated with none whereas the groups treated with HF4 showed similar morphology in respect of the number of lipid droplets as well as the general arrangement of hepatic tissue to normal group (See, FIG. 16).

Accordingly, it has been confirmed that the groups treated with HF2, HF3 and HF4, particularly, HF4 showed potent inhibiting effect on the morphological change of liver tissue caused by alcoholic fatty liver among them.

Experimental Example 6

The Change of Gene Expression of HMG-HMG-CoA

HMG-CoA (3-hydroxy-3-methylglutaryl-coenzyme A) reductase enzyme has been reported to play an important role in regulating the synthesis and dissociation pathway of cholesterol and the number of enzyme is increased by the uptake of alcohol resulting in increasing cholesterol synthesis. Accordingly, in order to investigate the effect of the inventive combined extract (HF2, HF3 and HF4) obtained in Example 2, on the change of gene expression of HMG-CoA-reductase, following experiment was performed according the method disclosed in the literature (Gene C. N, Reed C. H. Selective compensatory induction of hepatic HMG-CoA reductase in response to inhibition of cholesterol absorption. Exp. Biol. Mes. 231:559-569, 2006)

After performing the method similar to the method disclosed in 3-2, the liver was delivered and the RNA in liver tissue was isolated using by Trizole reagent (Gibco, BRL, USA). The extracted RNA was synthesized to cDNA using by M-MLV reverse transcriptase (Gibco, BRL, USA) and RT-PCR was performed using by primers against HMG-CoA reductase gene (Seq.#1(F): TGA GGG AAC CCT GAC ACT TA, Seq.#2(R): CTT CAA ATT TTG GGC ACT CA).
The Result of the Gene Expression of HMG-CoA As can be seen in FIG. 17, the control group (1.852) treated with 1% cholesterol and 35% alcohol showed increased amount of gene expression of HMG-CoA comparing with normal group treated with none (0.805) whereas the groups treated with HF2, HF3 and HF4 (HF2: 1.633, HF3: 1.290 and HF4: 1.224) showed about 1.5-folds reduced level of gene expression comparing with control group.

Figure 17:
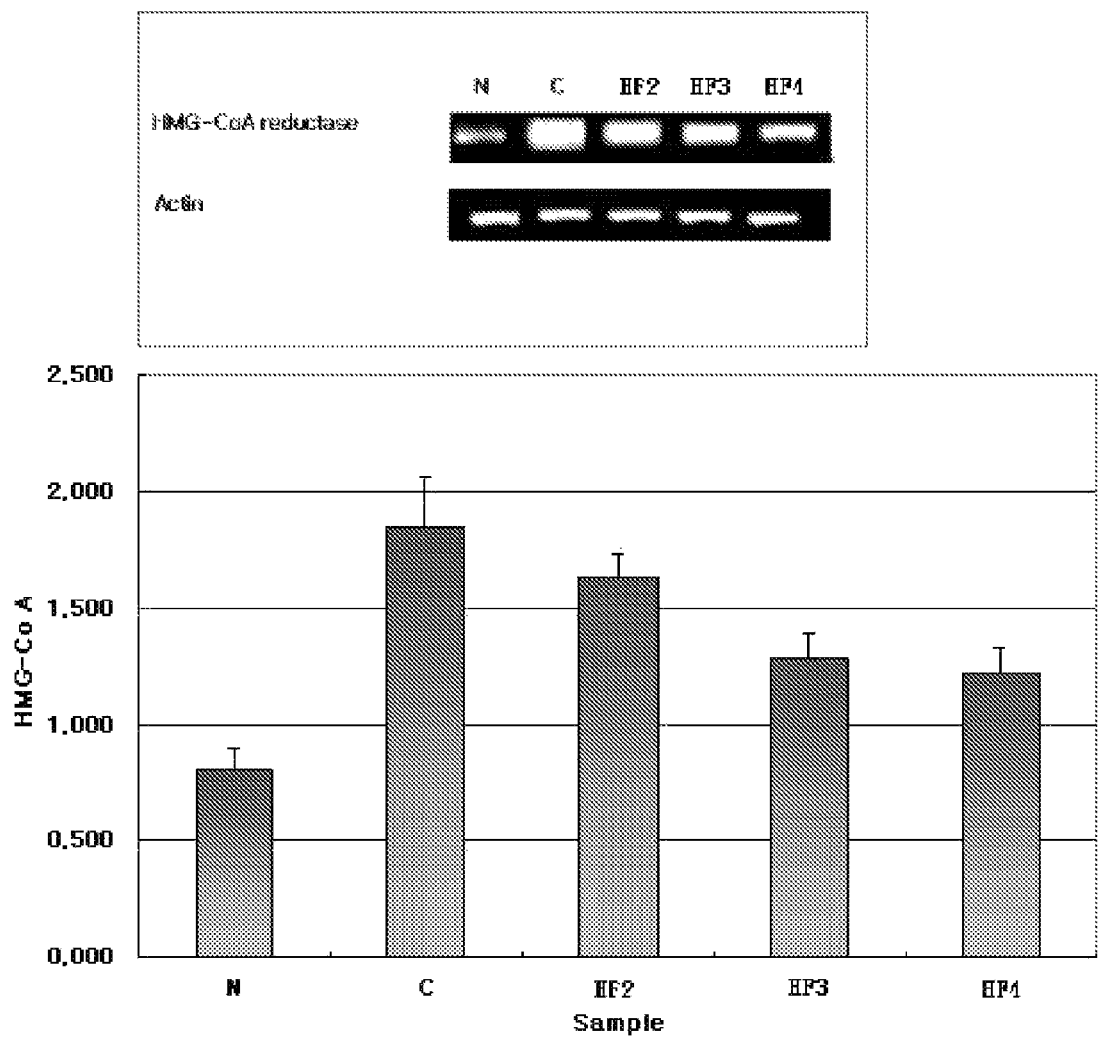
FIG. 17 represents the effect on the gene expression change of HMG-CoA reductase of the combined extract prepared in Example 2 in alcohol-induced fatty liver of rats.

Accordingly, it has been confirmed that the groups treated with HF2, HF3 and HF4, particularly, HF4 showed potent inhibiting effect on the gene expression of liver tissue caused by alcoholic fatty liver resulting in decreasing the production of cholesterol among them (See, FIG. 17).

Experimental Example 7

Evaluation of Acute Toxicity

To examine the toxicity of the inventive extract, acute toxicity tests were performed on rats.

The 15 male and female SD rats were divided with 3 groups and three dosages of inventive extract, i.e., 1 g/kg, 2 g/kg and 5 g/kg were administered to each 5 rats for 14 days and water was treated to the control group. The symptom of toxicity was observed for 4 weeks such as the change of weight, the hematological analysis and histological test.

As a result of experiment, there was no death example of the rats administered with inventive extract and there was no significant abnormality in the gain of weight, and the histological test etc. In accordance with above results, it was confirmed that the inventive extracts were safe.

Hereinafter, the formulating methods and kinds of excipients will be described, but the present invention is not limited to them. The representative preparation examples were described as follows.

Preparation of Injection

| HF4 | 100 mg |
| Sodium metabisulfite | 3.0 mg |
| Methyl paraben | 0.8 mg |
| Propyl paraben | 0.1 mg |
| Distilled water for injection | optimum amount |

Injection preparation was prepared by dissolving active component, controlling pH to about 7.5 and then filling all the components in 2 ml ample and sterilizing by conventional injection preparation method.

Preparation of Powder

| HF3 | 500 mg |
| Corn Starch | 100 mg |
| Lactose | 100 mg |
| Talc | 10 mg |

Powder preparation was prepared by mixing above components and filling sealed package.

Preparation of Tablet

| HF2 | 200 mg |
| Corn Starch | 100 mg |
| Lactose | 100 mg |
| Magnesium stearate | optimum amount |

Tablet preparation was prepared by mixing above components and entabletting.

Preparation of Capsule

| HF1 | 100 mg |
| Lactose | 50 mg |
| Corn starch | 50 mg |
| Talc | 2 mg |
| Magnesium stearate | optimum amount |

Tablet preparation was prepared by mixing above components and filling gelatin capsule by conventional gelatin preparation method.

Preparation of Liquid

| HF2 | 1000 mg |
| Sugar | 20 g |
| Polysaccharide | 20 g |
| Lemon flavor | 20 g |

Liquid preparation was prepared by dissolving active component, and then filling all the components in 1000 ml ample and sterilizing by conventional liquid preparation method.

Preparation of Health Food

| HF3 | 1000 mg |
| Vitamin mixture | optimum amount |
| Vitamin A acetate | 70 mg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 mg |
| Vitamin C | 10 mg |
| Biotin | 10 mg |
| Amide nicotinic acid | 1.7 mg |
| Folic acid | 50 mg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above mentioned vitamin and mineral mixture may be varied in many ways. Such variations are not to be regarded as a departure from the spirit and scope of the present invention.

Preparation of Health Beverage

| HF4 | 1000 mg |
| Citric acid | 1000 mg |
| Oligosaccharide | 100 g |
| Apricot concentration | 2 g |
| Taurine | 1 g |
| Distilled water | 900 ml |

Health beverage preparation was prepared by dissolving active component, mixing, stirred at 85° C. for 1 hour, filtered and then filling all the components in 1000 ml ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

The combined herb composition according to the present invention shows potent inhibiting effect on the level of increased GOT, GPT, cholesterol, triglyceride, LDL-cholesterol as well as increasing effect on the level of reduced HDL-cholesterol together with preventing and treating liver cirrhosis and fatty liver.

The inventive compositions according to the present invention are useful in the prevention and treatment of the liver diseases and can be used as safe and efficient hepato-protective agent.

Sequence List Text

SEQ ID NO. 1:   TGA GGG AAC CCT GAC ACT TA
SEQ ID NO. 2:   CTT CAA ATT TGG GCA CTC CA

The invention claimed is:

1. A method of treating acute hepatitis or chronic hepatitis in a mammal in need thereof consisting of administering to said mammal an effective amount of a composition consisting of an extract obtained from the following combination of herbs:
   (a) *Coriolus versicolor*;
   (b) *Astragalus membranaceus Bunge*; and
   (c) at least one herb selected from the group consisting of *Schisandra chinensis* and *Artemisia capillaris*; and
   a pharmaceutically acceptable carrier.

2. The method of claim 1, wherein said extract is obtained from a combination of *Coriolus versicolor, Astragalus membranaceus Bunge* and *Schisandra chinensis* with the mixed ratio based on the dried weight of each herb (w/w %) ranging from 0.1-10:0.1-10:1.

3. The method of claim 1, wherein said extract is obtained from a combination of *Coriolus versicolor, Astragalus membranaceus Bunge*, and *Artemisia capillaris* with the mixed ratio based on the dried weight of each herb (w/w %) ranging from 0.1-10:0.1-10:1.

4. The method of claim 1, wherein said extract is obtained from a combination of *Coriolus versicolor, Astragalus membranaceus Bunge, Schisandra chinensis*, and *Artemisia capillaris* with the mixed ratio based on the dried weight of each herb (w/w %) ranging from 0.1-10:0.1-10:0.1-10:1.

5. The method of claim 1, wherein said extract is selected from the group consisting of a crude extract, a lower alcohol insoluble fraction extract, and a non-polar solvent soluble extract.

6. The method of claim 5, wherein the non-polar solvent is selected from the group consisting of hexane, chloroform, dichloromethane and ethyl acetate.

7. The method of claim 5, wherein said crude extract is selected from the group consisting of an extract soluble in distilled water, a C1-C4 lower alcohol and mixtures thereof.

8. The method of claim 7, wherein the C1-C4 lower alcohol is selected from the group consisting of methanol and ethanol.

9. The method of claim 5, wherein said lower alcohol insoluble fraction extract is prepared by the steps:
   extracting the herbs with a solution of a mixture of a lower alcohol and water,
   fractionating the resulting extract into a lower alcohol soluble fraction and lower alcohol insoluble fraction; and
   collecting the lower alcohol insoluble fraction extract.

10. The method of claim 5, wherein said non-polar solvent soluble extract is prepared by the steps:
    fractionating the crude extract with a non-polar solvent; and
    collecting the non-polar solvent soluble extract.

11. The method of claim 1, wherein said extract is prepared by a process comprising the steps of:
    washing, drying and mixing the herbs in the proper ratio (w/w), pulverizing the herbs;
    mixing the pulverized herbs with 5 to 20-fold volume of a solution selected from the group consisting of distilled water, alcohol, methanol, ethanol and mixtures thereof, and
    enfleuraging by a method selected from the group consisting of heating at a temperature ranging from 0° C. to room temperature for a period ranging from 12 hours to 48 hours and heating 2 to 5 times at a temperature from 80° C. to 120° C. for a period ranging from 1 to 24 hours to obtain an extract solution;

filtering and concentrating the extract solution at 80° C. to 120° C. under reduced pressure, whereby said concentrating is by azeotropic distillation with a volume of 10 to 60-fold water, 1 to 5 times; and drying the concentrated extract solution by freeze drying or by vacuum drying to obtain said extract.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Homo sapiens

<400> SEQUENCE: 1
tgagggaacc ctgacactta                                               20

<210> SEQ ID NO 2
<211> LENGTH: 20
<212> TYPE: DNA
<213> ORGANISM: Homo sapiens

<400> SEQUENCE: 2
cttcaaattt tgggcactca                                               20